United States Patent
Cabiri (10) Patent No.: US 10,071,196 B2
(45) Date of Patent: Sep. 11, 2018

(54) METHOD FOR SELECTIVELY POWERING A BATTERY-OPERATED DRUG-DELIVERY DEVICE AND DEVICE THEREFOR

(75) Inventor: Oz Cabiri, Macabim Reut (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 431 days.

(21) Appl. No.: 13/472,112

(22) Filed: May 15, 2012

(65) Prior Publication Data

US 2013/0310753 A1    Nov. 21, 2013

(51) Int. Cl.
*A61M 5/142*   (2006.01)
*A61M 5/20*   (2006.01)

(52) U.S. Cl.
CPC .......... *A61M 5/14248* (2013.01); *A61M 2005/14252* (2013.01); *A61M 2005/2073* (2013.01); *A61M 2205/8206* (2013.01)

(58) Field of Classification Search
None
See application file for complete search history.

(56) References Cited

U.S. PATENT DOCUMENTS

| | | |
|---|---|---|
| 1,795,630 A | 3/1931 | Wilson |
| 2,860,635 A | 11/1958 | Wilburn |
| 3,203,269 A | 8/1965 | Perrine |
| 3,212,685 A | 10/1965 | Richard et al. |
| 3,794,028 A | 2/1974 | Mueller et al. |
| 3,994,295 A | 11/1976 | Wulff |
| 4,195,636 A | 4/1980 | Behnke |
| 4,218,724 A | 8/1980 | Kaufman |
| 4,273,122 A | 6/1981 | Whitney et al. |

(Continued)

FOREIGN PATENT DOCUMENTS

| | | |
|---|---|---|
| CN | 1224341 A | 7/1999 |
| CN | 1747683 A | 3/2006 |

(Continued)

OTHER PUBLICATIONS

Office Action dated Jan. 8, 2013 in JP Application No. 2010-527595.

(Continued)

*Primary Examiner* — Maria J Laios
(74) *Attorney, Agent, or Firm* — Panitch Schwarze Belisario & Nadel LLP (57) ABSTRACT

A method for selectively powering a battery-operated drug-delivery device, the device having a battery and a battery circuit, the method comprising: providing a battery isolator in a first position whereat it interrupts a battery circuit, whereby no power is provided to the device; and activating a fastening mechanism configured for fastening the device to a user, the activating causing the battery circuit to be uninterrupted by the isolator, such that power is provided to the device. Additionally, there is provided a selectively powered battery-operated drug-delivery device, comprising: a selectively-removable isolator disposed in a first position whereat it interrupts a battery circuit; the isolator movable to a second position whereat the battery circuit is uninterrupted by the isolator; and a mechanism for fastening the device to a user, activation of the fastening mechanism moving the isolator from the first position to the second position.

9 Claims, 5 Drawing Sheets

(56) References Cited

U.S. PATENT DOCUMENTS

| | | | |
|---|---|---|---|
| 4,300,554 A | 11/1981 | Hessberg et al. |
| 4,403,987 A | 9/1983 | Gottinger |
| 4,435,173 A | 3/1984 | Siposs et al. |
| 4,465,478 A | 8/1984 | Sabelman et al. |
| 4,565,543 A | 1/1986 | Bekkering et al. |
| 4,585,439 A | 4/1986 | Michel |
| 4,599,082 A | 7/1986 | Grimard |
| 4,601,702 A | 7/1986 | Hudson |
| 4,685,903 A | 8/1987 | Cable et al. |
| 4,698,055 A | 10/1987 | Sealfon |
| 4,810,215 A | 3/1989 | Kaneko |
| 4,850,966 A | 7/1989 | Grau et al. |
| 4,867,743 A | 9/1989 | Vaillancourt |
| 4,886,499 A | 12/1989 | Cirelli et al. |
| 4,919,596 A | 4/1990 | Slate et al. |
| 4,929,241 A | 5/1990 | Kulli |
| 4,950,246 A | 8/1990 | Muller |
| D322,671 S | 12/1991 | Szwarc |
| 5,109,850 A | 5/1992 | Blanco et al. |
| 5,112,317 A | 5/1992 | Michel |
| 5,131,816 A | 7/1992 | Brown et al. |
| 5,190,521 A | 3/1993 | Hubbard et al. |
| 5,254,096 A | 10/1993 | Rondelet et al. |
| 5,300,045 A | 4/1994 | Plassche, Jr. |
| 5,342,313 A | 8/1994 | Campbell et al. |
| 5,348,544 A | 9/1994 | Sweeney et al. |
| 5,366,498 A | 11/1994 | Brannan et al. |
| 5,383,865 A | 1/1995 | Michel |
| 5,478,315 A | 12/1995 | Brothers et al. |
| 5,482,446 A | 1/1996 | Williamson et al. |
| 5,496,274 A | 3/1996 | Graves et al. |
| 5,501,665 A | 3/1996 | Jhuboo et al. |
| 5,505,709 A | 4/1996 | Funderburk et al. |
| 5,562,686 A | 10/1996 | Sauer et al. |
| 5,593,390 A | 1/1997 | Castellano et al. |
| 5,616,132 A | 4/1997 | Newman |
| 5,643,218 A | 7/1997 | Lynn et al. |
| 5,645,955 A | 7/1997 | Maglica |
| 5,647,853 A | 7/1997 | Feldmann et al. |
| 5,662,678 A | 9/1997 | Macklin |
| 5,672,160 A | 9/1997 | Osterlind et al. |
| 5,690,618 A | 11/1997 | Smith et al. |
| D393,314 S | 4/1998 | Meisner et al. |
| 5,766,186 A | 6/1998 | Faraz et al. |
| 5,795,675 A | 8/1998 | Maglica |
| 5,800,420 A | 9/1998 | Gross et al. |
| 5,807,375 A | 9/1998 | Gross et al. |
| 5,814,020 A | 9/1998 | Gross |
| 5,836,920 A | 11/1998 | Robertson |
| 5,848,991 A | 12/1998 | Gross et al. |
| 5,851,197 A | 12/1998 | Marano et al. |
| 5,858,001 A | 1/1999 | Tsals et al. |
| 5,858,008 A | 1/1999 | Capaccio |
| 5,868,710 A | 2/1999 | Battiato et al. |
| 5,931,814 A | 8/1999 | Alex et al. |
| 5,941,850 A | 8/1999 | Shah et al. |
| 5,948,392 A | 9/1999 | Haslwanter et al. |
| 5,954,697 A | 9/1999 | Srisathapat et al. |
| 5,957,895 A | 9/1999 | Sage et al. |
| 5,968,011 A | 10/1999 | Larsen et al. |
| 5,993,423 A | 11/1999 | Choi |
| 6,004,297 A | 12/1999 | Steenfeldt-Jensen et al. |
| 6,033,245 A | 3/2000 | Yamkovoy |
| 6,033,377 A | 3/2000 | Rasmussen et al. |
| 6,064,797 A | 5/2000 | Crittendon et al. |
| 6,074,369 A | 6/2000 | Sage et al. |
| 6,149,614 A | 11/2000 | Dunshee et al. |
| 6,186,982 B1 | 2/2001 | Gross et al. |
| 6,200,289 B1 | 3/2001 | Hochman et al. |
| 6,200,296 B1 | 3/2001 | Dibiasi et al. |
| 6,224,569 B1 | 5/2001 | Brimhall |
| 6,248,093 B1 | 6/2001 | Moberg |
| 6,277,095 B1 | 8/2001 | Kriesel et al. |
| 6,277,098 B1 | 8/2001 | Klitmose et al. |
| 6,277,099 B1 | 8/2001 | Strowe et al. |
| 6,287,283 B1 | 9/2001 | Ljunggreen et al. |
| 6,293,925 B1 | 9/2001 | Safabash et al. |
| 6,302,633 B1 | 10/2001 | Poe |
| 6,336,729 B1 | 1/2002 | Pavelle et al. |
| 6,345,968 B1 | 2/2002 | Shupe |
| 6,377,848 B1 * | 4/2002 | Garde et al. ............ 604/20 |
| 6,391,005 B1 | 5/2002 | Lum et al. |
| 6,423,029 B1 | 7/2002 | Elsberry |
| D465,026 S | 10/2002 | May et al. |
| 6,458,102 B1 | 10/2002 | Mann et al. |
| 6,485,461 B1 | 11/2002 | Mason et al. |
| 6,485,465 B2 | 11/2002 | Moberg et al. |
| 6,500,150 B1 | 12/2002 | Gross et al. |
| 6,503,231 B1 | 1/2003 | Prausnitz et al. |
| 6,511,336 B1 | 1/2003 | Turek et al. |
| 6,517,517 B1 | 2/2003 | Farrugia et al. |
| D471,274 S | 3/2003 | Diaz et al. |
| D471,983 S | 3/2003 | Hippolyte et al. |
| 6,558,351 B1 | 5/2003 | Steil et al. |
| 6,589,229 B1 | 7/2003 | Connelly et al. |
| 6,595,956 B1 | 7/2003 | Gross et al. |
| 6,595,960 B2 | 7/2003 | West et al. |
| 6,645,181 B1 | 11/2003 | Lavi et al. |
| 6,652,482 B2 | 11/2003 | Hochman |
| 6,656,158 B2 | 12/2003 | Mahoney et al. |
| 6,656,159 B2 | 12/2003 | Flaherty |
| 6,659,980 B2 | 12/2003 | Moberg et al. |
| 6,673,033 B1 | 1/2004 | Sciulli et al. |
| 6,679,862 B2 | 1/2004 | Diaz et al. |
| 6,689,118 B2 | 2/2004 | Alchas et al. |
| 6,699,218 B2 | 3/2004 | Flaherty et al. |
| 6,722,916 B2 | 4/2004 | Buccinna et al. |
| 6,743,211 B1 | 6/2004 | Prausnitz et al. |
| 6,749,587 B2 | 6/2004 | Flaherty |
| 6,752,787 B1 | 6/2004 | Causey, III et al. |
| 6,768,425 B2 | 7/2004 | Flaherty et al. |
| 6,786,890 B2 | 9/2004 | Preuthun et al. |
| 6,800,071 B1 | 10/2004 | McConnell et al. |
| 6,805,687 B2 | 10/2004 | Dextradeur et al. |
| 6,824,529 B2 | 11/2004 | Gross et al. |
| 6,843,782 B2 | 1/2005 | Gross et al. |
| 6,854,620 B2 | 2/2005 | Ramey |
| 6,905,298 B1 | 6/2005 | Haring |
| 6,908,452 B2 | 6/2005 | Diaz et al. |
| 6,960,192 B1 | 11/2005 | Flaherty et al. |
| 6,997,727 B1 | 2/2006 | Legrady et al. |
| 7,001,360 B2 | 2/2006 | Veasey et al. |
| 7,034,223 B2 | 4/2006 | Fan et al. |
| 7,048,715 B2 | 5/2006 | Diaz et al. |
| 7,060,054 B2 | 6/2006 | Nissels |
| 7,060,059 B2 | 6/2006 | Keith et al. |
| 7,097,637 B2 | 8/2006 | Triplett et al. |
| 7,128,727 B2 | 10/2006 | Flaherty et al. |
| 7,144,384 B2 | 12/2006 | Gorman et al. |
| D544,092 S | 6/2007 | Lewis |
| 7,225,694 B2 | 6/2007 | Said |
| 7,247,149 B2 | 7/2007 | Beyerlein |
| 7,250,037 B2 | 7/2007 | Shermer et al. |
| 7,267,669 B2 | 9/2007 | Staunton et al. |
| 7,291,132 B2 | 11/2007 | DeRuntz et al. |
| 7,291,159 B2 | 11/2007 | Schmelzeisen-Redeker et al. |
| 7,303,549 B2 | 12/2007 | Flaherty et al. |
| 7,344,385 B2 | 3/2008 | Chen |
| 7,364,570 B2 | 4/2008 | Gerondale et al. |
| 7,390,314 B2 | 6/2008 | Stutz, Jr. et al. |
| 7,407,493 B2 | 8/2008 | Cane' |
| D578,210 S | 10/2008 | Muta et al. |
| 7,455,663 B2 | 11/2008 | Bikovsky |
| 7,465,290 B2 | 12/2008 | Reilly |
| 7,488,181 B2 | 2/2009 | van Haaster |
| 7,497,842 B2 | 3/2009 | Diaz et al. |
| 7,501,587 B2 | 3/2009 | English |
| 7,503,786 B2 | 3/2009 | Kato et al. |
| 7,530,964 B2 | 5/2009 | Lavi et al. |
| 7,547,281 B2 | 6/2009 | Hayes et al. |
| 7,565,208 B2 | 7/2009 | Harris et al. |
| 7,569,050 B2 | 8/2009 | Moberg et al. |
| D600,341 S | 9/2009 | Loerwald |
| 7,585,287 B2 | 9/2009 | Bresina et al. |

(56) References Cited

U.S. PATENT DOCUMENTS

| | | |
|---|---|---|
| 7,588,559 B2 | 9/2009 | Aravena et al. |
| 7,589,974 B2 | 9/2009 | Grady et al. |
| D602,155 S | 10/2009 | Foley et al. |
| D602,586 S | 10/2009 | Foley et al. |
| D604,835 S | 11/2009 | Conley |
| 7,628,770 B2 | 12/2009 | Ethelfeld |
| 7,628,772 B2 | 12/2009 | McConnell et al. |
| 7,628,782 B2 | 12/2009 | Adair et al. |
| 7,637,891 B2 | 12/2009 | Wall |
| 7,637,899 B2 | 12/2009 | Woolston et al. |
| 7,641,649 B2 | 1/2010 | Moberg et al. |
| 7,660,627 B2 | 2/2010 | McNichols et al. |
| 7,678,079 B2 | 3/2010 | Shermer et al. |
| 7,682,338 B2 | 3/2010 | Griffin |
| 7,686,787 B2 | 3/2010 | Moberg et al. |
| 7,699,829 B2 | 4/2010 | Harris et al. |
| 7,699,833 B2 | 4/2010 | Moberg et al. |
| 7,704,088 B2 | 4/2010 | Sakamoto |
| 7,704,227 B2 | 4/2010 | Moberg et al. |
| 7,704,229 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,913 B2 | 5/2010 | Novak et al. |
| 7,722,574 B2 | 5/2010 | Toman et al. |
| 7,736,344 B2 | 6/2010 | Moberg et al. |
| 7,744,589 B2 | 6/2010 | Mounce et al. |
| 7,749,194 B2 | 7/2010 | Edwards et al. |
| 7,776,030 B2 | 8/2010 | Estes et al. |
| 7,780,637 B2 | 8/2010 | Jerde et al. |
| 7,789,857 B2 | 9/2010 | Moberg et al. |
| 7,801,599 B2 | 9/2010 | Young et al. |
| 7,806,868 B2 | 10/2010 | De Polo et al. |
| 7,828,528 B2 | 11/2010 | Estes et al. |
| 7,837,659 B2 | 11/2010 | Bush, Jr. et al. |
| 7,846,132 B2 | 12/2010 | Gravesen et al. |
| 7,854,723 B2 | 12/2010 | Hwang et al. |
| 7,857,131 B2 | 12/2010 | Vedrine |
| 7,879,025 B2 | 2/2011 | Jacobson et al. |
| 7,918,825 B2 | 4/2011 | O'Connor et al. |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,955,305 B2 | 6/2011 | Moberg et al. |
| 7,967,784 B2 | 6/2011 | Pongpairochana et al. |
| 7,967,795 B1 | 6/2011 | Cabiri |
| 7,981,105 B2 | 7/2011 | Adair et al. |
| 7,988,683 B2 | 8/2011 | Adair et al. |
| 7,993,300 B2 | 8/2011 | Nyholm et al. |
| 7,993,301 B2 | 8/2011 | Boyd et al. |
| 7,998,111 B2 | 8/2011 | Moberg et al. |
| 8,021,357 B2 | 9/2011 | Tanaka et al. |
| 8,025,658 B2 | 9/2011 | Chong et al. |
| 8,029,469 B2 | 10/2011 | Ethelfeld |
| 8,034,019 B2 | 10/2011 | Nair et al. |
| 8,038,666 B2 | 10/2011 | Triplett et al. |
| 8,057,431 B2 | 11/2011 | Woehr et al. |
| 8,057,436 B2 | 11/2011 | Causey et al. |
| 8,062,253 B2 | 11/2011 | Nielsen et al. |
| 8,066,694 B2 | 11/2011 | Wagener |
| D650,079 S | 12/2011 | Presta et al. |
| D650,903 S | 12/2011 | Kosinski et al. |
| 8,086,306 B2 | 12/2011 | Katzman et al. |
| D652,503 S | 1/2012 | Cameron et al. |
| 8,105,279 B2 | 1/2012 | Mernoe et al. |
| 8,114,046 B2 | 2/2012 | Covino et al. |
| 8,114,064 B2 | 2/2012 | Alferness et al. |
| 8,114,066 B2 | 2/2012 | Naef et al. |
| D657,462 S | 4/2012 | Siroky |
| 8,147,446 B2 | 4/2012 | Yodfat et al. |
| 8,152,764 B2 | 4/2012 | Istoc et al. |
| 8,152,770 B2 | 4/2012 | Reid |
| 8,152,779 B2 | 4/2012 | Cabiri |
| 8,152,793 B2 | 4/2012 | Keinanen et al. |
| 8,157,693 B2 | 4/2012 | Waksmundzki |
| 8,162,674 B2 | 4/2012 | Cho et al. |
| 8,162,923 B2 | 4/2012 | Adams et al. |
| 8,167,841 B2 | 5/2012 | Teisen-Simony et al. |
| 8,172,591 B2 | 5/2012 | Wertz |
| 8,172,804 B2 | 5/2012 | Bikovsky |
| 8,182,462 B2 | 5/2012 | Istoc et al. |
| 8,197,444 B1 | 6/2012 | Bazargan et al. |
| 8,206,351 B2 | 6/2012 | Sugimoto et al. |
| 8,221,356 B2 | 7/2012 | Enggaard et al. |
| 8,267,921 B2 | 9/2012 | Yodfat et al. |
| 8,287,520 B2 | 10/2012 | Drew et al. |
| 8,292,647 B1 | 10/2012 | McGrath et al. |
| 8,308,679 B2 | 11/2012 | Hanson et al. |
| 8,323,250 B2 | 12/2012 | Chong et al. |
| 8,372,039 B2 | 2/2013 | Mernoe et al. |
| 8,373,421 B2 | 2/2013 | Lindegger et al. |
| 8,409,142 B2 | 4/2013 | Causey et al. |
| 8,414,557 B2 | 4/2013 | Istoc et al. |
| 8,430,847 B2 | 4/2013 | Mernoe et al. |
| 8,465,455 B2 | 6/2013 | Cabiri |
| 8,469,942 B2 | 6/2013 | Kow et al. |
| 8,474,332 B2 | 7/2013 | Bente, IV et al. |
| 8,475,408 B2 | 7/2013 | Mernoe et al. |
| 8,479,595 B2 | 7/2013 | Vazquez et al. |
| 8,495,918 B2 | 7/2013 | Bazargan et al. |
| 8,496,862 B2 | 7/2013 | Zelkovich et al. |
| 8,512,287 B2 | 8/2013 | Cindrich et al. |
| 8,517,987 B2 | 8/2013 | Istoc et al. |
| 8,523,803 B1 | 9/2013 | Favreau |
| 8,556,856 B2 | 10/2013 | Bazargan et al. |
| 8,562,364 B2 | 10/2013 | Lin et al. |
| 8,574,216 B2 | 11/2013 | Istoc et al. |
| 8,603,026 B2 | 12/2013 | Favreau |
| 8,603,027 B2 | 12/2013 | Favreau |
| 8,628,510 B2 | 1/2014 | Bazargan et al. |
| 8,674,288 B2 | 3/2014 | Hanson et al. |
| 8,679,060 B2 | 3/2014 | Mernoe et al. |
| 8,690,855 B2 | 4/2014 | Alderete, Jr. et al. |
| 8,708,961 B2 | 4/2014 | Field et al. |
| 8,751,237 B2 | 6/2014 | Kubota |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian, Jr. et al. |
| 8,777,896 B2 | 7/2014 | Starkweather et al. |
| 8,777,924 B2 | 7/2014 | Kanderian, Jr. et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,790,295 B1 | 7/2014 | Sigg et al. |
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |
| 8,801,679 B2 | 8/2014 | Iio et al. |
| 8,810,394 B2 | 8/2014 | Kalpin |
| 8,814,379 B2 | 8/2014 | Griffiths et al. |
| 9,061,104 B2 | 6/2015 | Daniel |
| 9,061,110 B2 | 6/2015 | Avery et al. |
| 9,089,475 B2 | 7/2015 | Fangrow |
| 9,089,641 B2 | 7/2015 | Kavazov |
| 2001/0025168 A1 | 9/2001 | Gross et al. |
| 2001/0041869 A1 | 11/2001 | Causey et al. |
| 2002/0010423 A1 | 1/2002 | Gross et al. |
| 2002/0029018 A1 | 3/2002 | Jeffrey |
| 2002/0040208 A1 | 4/2002 | Flaherty et al. |
| 2002/0055711 A1 | 5/2002 | Lavi et al. |
| 2002/0065488 A1 | 5/2002 | Suzuki et al. |
| 2002/0107487 A1 | 8/2002 | Preuthun |
| 2002/0123740 A1 | 9/2002 | Flaherty et al. |
| 2002/0161332 A1 | 10/2002 | Ramey |
| 2002/0169215 A1 | 11/2002 | Meng |
| 2003/0009133 A1 | 1/2003 | Ramey |
| 2003/0125671 A1 | 7/2003 | Aramata et al. |
| 2003/0135159 A1 | 7/2003 | Daily et al. |
| 2003/0160683 A1 | 8/2003 | Blomquist |
| 2003/0171717 A1 | 9/2003 | Farrugia et al. |

(56) References Cited

U.S. PATENT DOCUMENTS

| | | |
|---|---|---|
| 2004/0010207 A1 | 1/2004 | Flaherty et al. |
| 2004/0092873 A1 | 5/2004 | Moberg |
| 2004/0116866 A1 | 6/2004 | Gorman et al. |
| 2004/0127857 A1 | 7/2004 | Shemesh et al. |
| 2004/0158172 A1 | 8/2004 | Hancock |
| 2004/0186419 A1 | 9/2004 | Cho |
| 2004/0260233 A1 | 12/2004 | Garibotto et al. |
| 2005/0033234 A1 | 2/2005 | Sadowski et al. |
| 2005/0065466 A1 | 3/2005 | Vedrine |
| 2005/0065472 A1 | 3/2005 | Cindrich et al. |
| 2005/0071487 A1 | 3/2005 | Lu et al. |
| 2005/0113761 A1 | 5/2005 | Faust et al. |
| 2005/0159706 A1 | 7/2005 | Wilkinson et al. |
| 2005/0171476 A1 | 8/2005 | Judson et al. |
| 2005/0171512 A1 | 8/2005 | Flaherty |
| 2005/0177136 A1 | 8/2005 | Miller |
| 2005/0197650 A1 | 9/2005 | Sugimoto et al. |
| 2005/0203461 A1 | 9/2005 | Flaherty et al. |
| 2005/0238507 A1 | 10/2005 | Dilanni et al. |
| 2005/0283114 A1 | 12/2005 | Bresina et al. |
| 2006/0013716 A1 | 1/2006 | Nason et al. |
| 2006/0030816 A1 | 2/2006 | Zubry |
| 2006/0095014 A1 | 5/2006 | Ethelfeld |
| 2006/0122577 A1 | 6/2006 | Poulsen et al. |
| 2006/0173406 A1 | 8/2006 | Hayes et al. |
| 2006/0173439 A1 | 8/2006 | Thorne et al. |
| 2006/0195029 A1 | 8/2006 | Shults et al. |
| 2006/0211982 A1 | 9/2006 | Prestrelski et al. |
| 2006/0229569 A1 | 10/2006 | Lavi et al. |
| 2006/0264889 A1 | 11/2006 | Moberg et al. |
| 2006/0264890 A1 | 11/2006 | Moberg et al. |
| 2006/0264894 A1 | 11/2006 | Moberg et al. |
| 2006/0270987 A1 | 11/2006 | Peter |
| 2006/0283465 A1 | 12/2006 | Nickel et al. |
| 2006/0293722 A1 | 12/2006 | Slatkine et al. |
| 2007/0021733 A1 | 1/2007 | Hansen et al. |
| 2007/0049865 A1 | 3/2007 | Radmer et al. |
| 2007/0073228 A1 | 3/2007 | Mernoe et al. |
| 2007/0118405 A1 | 5/2007 | Campbell et al. |
| 2007/0123819 A1 | 5/2007 | Mernoe et al. |
| 2007/0167912 A1 | 7/2007 | Causey et al. |
| 2007/0185449 A1 | 8/2007 | Mernoe |
| 2007/0197968 A1 | 8/2007 | Pongpairochana et al. |
| 2007/0203454 A1 | 8/2007 | Shermer et al. |
| 2007/0233038 A1 | 10/2007 | Pruitt et al. |
| 2007/0282269 A1 | 12/2007 | Carter et al. |
| 2008/0021439 A1 | 1/2008 | Brittingham et al. |
| 2008/0033367 A1 | 2/2008 | Haury et al. |
| 2008/0033369 A1 | 2/2008 | Kohlbrenner et al. |
| 2008/0033393 A1 | 2/2008 | Edwards et al. |
| 2008/0051711 A1 | 2/2008 | Mounce et al. |
| 2008/0051730 A1 | 2/2008 | Bikovsky |
| 2008/0059133 A1 | 3/2008 | Edwards et al. |
| 2008/0097381 A1 | 4/2008 | Moberg et al. |
| 2008/0108951 A1 | 5/2008 | Jerde et al. |
| 2008/0140006 A1 | 6/2008 | Eskuri et al. |
| 2008/0140018 A1 | 6/2008 | Enggaard et al. |
| 2008/0147004 A1 | 6/2008 | Mann et al. |
| 2008/0167641 A1 | 7/2008 | Hansen et al. |
| 2008/0188813 A1 | 8/2008 | Miller et al. |
| 2008/0208138 A1 | 8/2008 | Lim et al. |
| 2008/0215006 A1 | 9/2008 | Thorkild |
| 2008/0215015 A1 | 9/2008 | Cindrich et al. |
| 2008/0243087 A1 | 10/2008 | Enggaard et al. |
| 2008/0249473 A1 | 10/2008 | Rutti et al. |
| 2008/0262436 A1 | 10/2008 | Olson |
| 2008/0269687 A1 | 10/2008 | Chong et al. |
| 2008/0269723 A1 | 10/2008 | Mastrototaro et al. |
| 2008/0274630 A1 | 11/2008 | Shelton et al. |
| 2008/0294143 A1 | 11/2008 | Tanaka et al. |
| 2008/0306449 A1 | 12/2008 | Kristensen et al. |
| 2008/0312601 A1 | 12/2008 | Cane |
| 2008/0319416 A1 | 12/2008 | Yodfat et al. |
| 2009/0041805 A1 | 2/2009 | Walker |
| 2009/0048347 A1 | 2/2009 | Cohen et al. |
| 2009/0054750 A1 | 2/2009 | Jennewine |
| 2009/0069784 A1 | 3/2009 | Estes et al. |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093792 A1 | 4/2009 | Gross et al. |
| 2009/0093793 A1 | 4/2009 | Gross et al. |
| 2009/0105650 A1 | 4/2009 | Wiegel et al. |
| 2009/0124977 A1 | 5/2009 | Jensen |
| 2009/0143730 A1 | 6/2009 | De Polo et al. |
| 2009/0143735 A1 | 6/2009 | De Polo et al. |
| 2009/0149830 A1 | 6/2009 | Spector |
| 2009/0182277 A1 | 7/2009 | Carter |
| 2009/0204076 A1 | 8/2009 | Liversidge |
| 2009/0209896 A1* | 8/2009 | Selevan .................. 602/41 |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259176 A1 | 10/2009 | Yairi |
| 2009/0281585 A1 | 11/2009 | Katzman et al. |
| 2009/0299290 A1 | 12/2009 | Moberg |
| 2009/0299397 A1 | 12/2009 | Ruan et al. |
| 2009/0326459 A1 | 12/2009 | Shipway et al. |
| 2009/0326509 A1 | 12/2009 | Muse et al. |
| 2010/0030156 A1 | 2/2010 | Beebe et al. |
| 2010/0030198 A1 | 2/2010 | Beebe et al. |
| 2010/0049128 A1 | 2/2010 | McKenzie et al. |
| 2010/0049144 A1 | 2/2010 | McConnell et al. |
| 2010/0057057 A1 | 3/2010 | Hayter et al. |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0137831 A1 | 6/2010 | Tsals |
| 2010/0145303 A1 | 6/2010 | Yodfat et al. |
| 2010/0145305 A1 | 6/2010 | Alon |
| 2010/0162548 A1 | 7/2010 | Leidig |
| 2010/0168607 A1 | 7/2010 | Miesel |
| 2010/0168683 A1 | 7/2010 | Cabiri |
| 2010/0198157 A1 | 8/2010 | Gyrn et al. |
| 2010/0204657 A1 | 8/2010 | Yodfat et al. |
| 2010/0234767 A1 | 9/2010 | Sarstedt |
| 2010/0234805 A1 | 9/2010 | Kaufmann et al. |
| 2010/0234830 A1 | 9/2010 | Straessler et al. |
| 2010/0241065 A1 | 9/2010 | Moberg et al. |
| 2010/0264931 A1 | 10/2010 | Lindegger et al. |
| 2010/0274112 A1 | 10/2010 | Hoss et al. |
| 2010/0274192 A1 | 10/2010 | Mernoe |
| 2010/0280499 A1 | 11/2010 | Yodfat et al. |
| 2010/0331826 A1 | 12/2010 | Field et al. |
| 2011/0034900 A1 | 2/2011 | Yodfat et al. |
| 2011/0054399 A1 | 3/2011 | Chong et al. |
| 2011/0054400 A1 | 3/2011 | Chong et al. |
| 2011/0066131 A1 | 3/2011 | Cabiri |
| 2011/0125056 A1 | 5/2011 | Merchant |
| 2011/0160654 A1 | 6/2011 | Hanson et al. |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0172745 A1 | 7/2011 | Na et al. |
| 2011/0178472 A1 | 7/2011 | Cabiri |
| 2011/0201998 A1 | 8/2011 | Pongpairochana et al. |
| 2011/0238031 A1 | 9/2011 | Adair et al. |
| 2011/0245773 A1 | 10/2011 | Estes et al. |
| 2011/0270160 A1 | 11/2011 | Mernoe |
| 2011/0282282 A1 | 11/2011 | Lorenzen et al. |
| 2011/0282296 A1 | 11/2011 | Harms et al. |
| 2011/0295205 A1 | 12/2011 | Kaufmann et al. |
| 2011/0313238 A1 | 12/2011 | Reichenbach et al. |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022344 A1 | 1/2012 | Kube |
| 2012/0022499 A1 | 1/2012 | Anderson et al. |
| 2012/0029431 A1 | 2/2012 | Hwang et al. |

(56) References Cited

U.S. PATENT DOCUMENTS

| | | |
|---|---|---|
| 2012/0035546 A1 | 2/2012 | Cabiri |
| 2012/0041364 A1 | 2/2012 | Smith |
| 2012/0041414 A1 | 2/2012 | Estes et al. |
| 2012/0071828 A1 | 3/2012 | Tojo et al. |
| 2012/0096953 A1 | 4/2012 | Bente, IV et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0129362 A1 | 5/2012 | Hampo et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0226234 A1 | 9/2012 | Bazargan et al. |
| 2012/0259282 A1 | 10/2012 | Alderete, Jr. et al. |
| 2013/0012875 A1 | 1/2013 | Gross et al. |
| 2013/0068319 A1 | 3/2013 | Plumptre et al. |
| 2013/0085457 A1 | 4/2013 | Schiff et al. |
| 2013/0089992 A1 | 4/2013 | Yang |
| 2013/0096509 A1 | 4/2013 | Avery et al. |
| 2013/0110049 A1 | 5/2013 | Cronenberg et al. |
| 2013/0133438 A1 | 5/2013 | Kow et al. |
| 2013/0237953 A1 | 9/2013 | Kow et al. |
| 2013/0245595 A1 | 9/2013 | Kow et al. |
| 2013/0245596 A1 | 9/2013 | Cabiri et al. |
| 2013/0253419 A1 | 9/2013 | Favreau |
| 2013/0253420 A1 | 9/2013 | Favreau |
| 2013/0253421 A1 | 9/2013 | Favreau |
| 2013/0296799 A1 | 11/2013 | Degtiar et al. |
| 2013/0304021 A1 | 11/2013 | Cabiri et al. |
| 2013/0323699 A1 | 12/2013 | Edwards et al. |
| 2013/0331791 A1 | 12/2013 | Gross et al. |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0128807 A1 | 5/2014 | Moberg et al. |
| 2014/0128815 A1 | 5/2014 | Cabiri et al. |
| 2014/0128835 A1 | 5/2014 | Moberg et al. |
| 2014/0135692 A1 | 5/2014 | Alderete, Jr. et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete, Jr. et al. |
| 2014/0194819 A1 | 7/2014 | Maule et al. |
| 2014/0194854 A1 | 7/2014 | Tsals |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0213975 A1 | 7/2014 | Clemente et al. |
| 2014/0236087 A1 | 8/2014 | Alderete, Jr. et al. |
| 2014/0261758 A1 | 9/2014 | Wlodarczyk et al. |

FOREIGN PATENT DOCUMENTS

| | | |
|---|---|---|
| CN | 1863566 A | 11/2006 |
| CN | 1929884 A | 3/2007 |
| CN | 101090749 A | 12/2007 |
| CN | 101460207 A | 6/2009 |
| CN | 101970033 A | 2/2011 |
| CN | 201941304 U | 8/2011 |
| CN | 102186733 A | 9/2011 |
| CN | 102256657 A | 11/2011 |
| DE | 1064693 B | 9/1959 |
| EP | 0017412 A1 | 10/1980 |
| EP | 0222656 A1 | 5/1987 |
| EP | 0401179 A1 | 12/1990 |
| EP | 1530979 A1 | 5/2005 |
| EP | 1666080 A1 | 6/2006 |
| EP | 2060606 A1 | 5/2009 |
| EP | 2498589 A1 | 9/2012 |
| JP | H07-194701 A | 8/1995 |
| JP | H09-505758 A | 6/1997 |
| JP | 2001-512992 A | 8/2001 |
| JP | 2002-505601 A | 2/2002 |
| JP | 2002-507459 A | 3/2002 |
| JP | 2002-528676 A | 9/2002 |
| JP | 2003-501157 A | 1/2003 |
| JP | 2003-527138 A | 9/2003 |
| JP | 2003-534061 A | 11/2003 |
| JP | 2004-501721 A | 1/2004 |
| JP | 2004-512100 A | 4/2004 |
| JP | 2005-523127 A | 8/2005 |
| JP | 2005-270629 A | 10/2005 |
| JP | 2007-509661 A | 4/2007 |
| JP | 2008-534131 A | 8/2008 |
| JP | 2008-220961 A | 9/2008 |
| JP | 2009-502273 A | 1/2009 |
| WO | 9009202 A1 | 8/1990 |
| WO | 9307922 A1 | 4/1993 |
| WO | 9407553 A1 | 4/1994 |
| WO | 9513838 A1 | 5/1995 |
| WO | 9609083 A1 | 3/1996 |
| WO | 9632975 A1 | 10/1996 |
| WO | 9700091 A1 | 1/1997 |
| WO | 9710012 A1 | 3/1997 |
| WO | 9733638 A1 | 9/1997 |
| WO | 9857683 A1 | 12/1998 |
| WO | 9929151 A1 | 6/1999 |
| WO | 9959665 A1 | 11/1999 |
| WO | 0025844 A1 | 5/2000 |
| WO | 0187384 A1 | 11/2001 |
| WO | 0189607 A2 | 11/2001 |
| WO | 0189613 A1 | 11/2001 |
| WO | 0202165 A2 | 1/2002 |
| WO | 0234315 A1 | 5/2002 |
| WO | 0272182 A1 | 9/2002 |
| WO | 03090833 A1 | 11/2003 |
| WO | 2004032990 A2 | 4/2004 |
| WO | 2004105841 A1 | 12/2004 |
| WO | 2005018703 A2 | 3/2005 |
| WO | 2005037350 A2 | 4/2005 |
| WO | 2006037434 A1 | 4/2006 |
| WO | 06069380 A1 | 6/2006 |
| WO | 2006102676 A1 | 9/2006 |
| WO | 2006104806 A2 | 10/2006 |
| WO | 2007051563 A1 | 5/2007 |
| WO | 2007056504 A1 | 5/2007 |
| WO | 2008001377 A2 | 1/2008 |
| WO | 2008014908 A1 | 2/2008 |
| WO | 2008057976 A2 | 5/2008 |
| WO | 2008072229 A2 | 6/2008 |
| WO | 2008076459 A1 | 6/2008 |
| WO | 2008078318 A2 | 7/2008 |
| WO | 2009044401 | 4/2009 |
| WO | 2009046989 A2 | 4/2009 |
| WO | WO 2009/125398 A2 * | 10/2009 ............ A61M 5/14 |
| WO | 2009144085 A2 | 12/2009 |
| WO | 2010078227 A1 | 7/2010 |
| WO | 2010078242 A1 | 7/2010 |
| WO | 2011075105 A1 | 6/2011 |
| WO | 2011090955 A1 | 7/2011 |
| WO | 2011090956 A2 | 7/2011 |
| WO | 2011156373 A1 | 12/2011 |
| WO | 2012032411 A2 | 3/2012 |
| WO | 2012040528 A1 | 3/2012 |
| WO | 2012160157 A1 | 11/2012 |
| WO | 2013/173092 A1 | 11/2013 |
| WO | 2014/070453 A1 | 5/2014 |

OTHER PUBLICATIONS

Int'l Preliminary Report on Patentability dated Feb. 7, 2013 in Int'l Application No. PCT/US2011/021604.
Int'l Preliminary Report on Patentability dated Feb. 7, 2013 in Int'l Application No. PCT/US2011/021605.
U.S. Appl. No. 13/643,470 by Alon, filed Oct. 25, 2012.
U.S. Appl. No. 13/733,516 by Cabiri, filed Jan. 3, 2013.
Office Action dated Dec. 17, 2013 in JP Application No. 2012-529808.
Office Action dated Dec. 10, 2013 in CN Application No. 201180006567.4.

(56) References Cited

OTHER PUBLICATIONS

Office Action dated Jan. 8, 2014 in U.S. Appl. No. 13/521,167 by Cabiri.
U.S. Appl. No. 29/479,307 by Norton, filed Jan. 14, 2014.
English translation of an Office Action dated Jan. 30, 2013 in CN Application No. 200880117084.X.
Int'l Preliminary Report on Patentability dated Aug. 2, 2012 in Int'l Application No. PCT/US2011/021604.
Office Action dated Oct. 9, 2013 in IL Application No. 208634.
Office Action dated Nov. 5, 2013 in JP Application No. 2010-527595.
Office Action dated Sep. 29, 2013 in CN Application No. 201080040968.7.
Office Action dated Nov. 4, 2013 in EP Application No. 11 709 234.6.
Int'l Search Report and Written Opinion dated Jul. 26, 2013 in Int'l Application No. PCT/US2012/039465.
Int'l Search Report and Written Opinion dated Aug. 5, 2013 in Int'l Application No. PCT/US2013/033118.
U.S. Appl. No. 13/964,651 by Gross, filed Aug. 12, 2013.
Office Action dated Aug. 15, 2013 in CN Application No. 200880117084.X.
Daikyo Crystal Zenith® polymer, Manufactured by Daikyo Seiko, Ltd.
Copaxone®, Manufactured by Teva Pharmaceutical Industries Ltd.
U.S. Appl. No. 14/193,692 by Gross, filed Feb. 28, 2014.
Office Action dated Feb. 4, 2014 in EP Application No. 11 707 942.6.
English translation of an Office Action dated Mar. 5, 2014 in CN Application No. 200880117084.X.
Int'l Search Report and Written Opinion dated Apr. 3, 2014 in Int'l Application No. PCT/US2013/078040.
Extended European Search Report dated Mar. 27, 2014 in EP Application No. 14154717.4.
Office Action dated Feb. 28, 2014 in CN Application No. 201180006571.0.
U.S. Appl. No. 13/873,335 by Filman, filed Apr. 30, 2013.
U.S. Appl. No. 13/892,905 by Cabiri, filed May 13, 2013.
U.S. Appl. No. 13/874,121 by Degtiar, filed Apr. 30, 2013.
U.S. Appl. No. 13/874,085 by Cabiri, filed Apr. 30, 2013.
U.S. Appl. No. 13/874,017 by Cabiri, filed Apr. 30, 2013.
Office Action dated Jun. 3, 2014 in JP Application No. 2010-527595.
Office Action dated Jul. 7, 2014 in U.S. Appl. No. 12/244,666 by Gross.
Int'l Search Report and Written Opinion dated Jul. 31, 2014 in Int'l Application No. PCT/US2014/033598.
U.S. Appl. No. 14/258,661 by Cabiri, filed Apr. 22, 2014.
Int'l Search Report and Written Opinion dated Jan. 7, 2014 in Int'l Application No. PCT/US2013/065211.
Office Action dated May 18, 2016 in U.S. Appl. No. 13/667,739 by Cabiri.
Office Action dated Sep. 9, 2015 in U.S. Appl. No. 13/643,470 by Alon.
U.S. Appl. No. 14/850,450 by Gross, filed Sep. 10, 2015.
U.S. Appl. No. 14/861,478 by Cabiri, filed Sep. 22, 2015.
U.S. Appl. No. 14/880,673 by Cabiri, filed Oct. 12, 2015.
Office Action dated Sep. 30, 2015 in U.S. Appl. No. 13/667,739 by Cabiri.
Office Action dated Sep. 18, 2015 in U.S. Appl. No. 13/874,085 by Cabiri.
U.S. Appl. No. 14/683,193 by Cabiri, filed Apr. 10, 2015.
Office Action dated Feb. 20, 2015 in U.S. Appl. No. 13/521,181 by Cabiri.
Office Action dated Feb. 24, 2015 in U.S. Appl. No. 14/258,661 by Cabiri.
U.S. Appl. No. 14/638,525 by Filman, filed Mar. 4, 2015.
Extended European Search Report dated Feb. 23, 2015 in EP Application No. 14166596.8.
Office Action dated Mar. 10, 2015 in U.S. Appl. No. 13/643,470 by Alon.
Office Action dated Mar. 10, 2015 in U.S. Appl. No. 12/244,666 by Gross.
Extended European Search Report dated Feb. 23, 2015 in EP Application No. 14166591.9.
Office Action dated Mar. 10, 2015 in CN Application No. 201180006567.4.
Office Action dated Mar. 31, 2015 in JP Application No. 2012-550068.
Office Action dated Jul. 31, 2015 in U.S. Appl. No. 13/521,181 by Cabiri.
Office Action dated Aug. 13, 2015 in U.S. Appl. No. 14/553,399 by Cabiri.
Int'l Preliminary Report on Patentability dated Jul. 16, 2015 in Int'l Application No. PCT/US2013/078040.
Notice of Allowance dated Aug. 24, 2015 in U.S. Appl. No. 29/479,307 by Norton.
Extended European Search Report dated Aug. 7, 2014 in EP Application No. 1417477.4.
Office Action dated Aug. 6, 2014 in EP Application No. 11 707 942.6.
Office Action dated Sep. 2, 2014 in JP Application No. 2012-550069.
Office Action dated Sep. 2, 2014 in JP Application No. 2012-550068.
Office Action dated Aug. 26, 2014 in CN Application No. 201180006567.4.
Int'l Preliminary Report on Patentability dated Oct. 9, 2014 in Int'l Application No. PCT/US2013/033118.
Office Action dated Oct. 9, 2014 in U.S. Appl. No. 13/873,335.
Int'l Preliminary Report on Patentability dated May 14, 2015 in Int'l Application No. PCT/US2013/065211.
Office Action dated May 7, 2015 in JP Application No. 2012-550069.
Office Action dated May 13, 2015 in CN Application No. 201380025566.3.
U.S. Appl. No. 14/715,791 by Cabiri, filed May 19, 2015.
U.S. Appl. No. 14/725,009 by Bar-El, filed May 29, 2015.
Office Action dated May 1, 2015 in U.S. Appl. No. 14/638,525 by Filman.
Office Action dated Jun. 4, 2015 in U.S. Appl. No. 13/667,739 by Cabiri.
U.S. Appl. No. 14/593,051 by Gross, filed Jan. 9, 2015.
Office Action dated Nov. 5, 2014 in U.S. Appl. No. 13/643,470 by Alon.
U.S. Appl. No. 14/553,399 by Cabiri, filed Nov. 25, 2014.
Office Action dated Nov. 2, 2014 in CN Application No. 201180006571.0.
Office Action dated Nov. 21, 2014 in U.S. Appl. No. 13/429,840 by Cabiri.
Int'l Preliminary Report on Patentability dated Nov. 27, 2014 in Int'l Application No. PCT/US2013/039465.
Daikyo Crystal Zenith® polymer, Manufactured by Daikyo Seiko, Ltd. Printed Jan. 6, 2009.
Copaxone®, Manufactured by Teva Pharmaceutical Industries Ltd. printed Jan. 6, 2009.
Int'l Search Report dated May 13, 2009 in Int'l Application No. PCT/IL2008/001312.
Int'l Preliminary Report on Patentability dated Apr. 7, 2010 in Int'l Application No. PCT/IL2008/001312; Written Opinion.
Int'l Search Report dated Apr. 26, 2010 in Int'l Application No. PCT/US2009/069552.
Office Action dated Apr. 5, 2010 in U.S. Appl. No. 12/244,666.
Office Action dated Sep. 21, 2010 in U.S. Appl. No. 12/244,666.
Office Action dated Apr. 5, 2010 in U.S. Appl. No. 12/244,688.
Office Action dated Sep. 2, 2010 in U.S. Appl. No. 12/244,688.
Office Action dated Sep. 30, 2010 in U.S. Appl. No. 12/689,250.
Int'l Search Report dated Jan. 12, 2011 in Int'l Application No. PCT/US2010/048556; Written Opinion.
International Preliminary Report on Patentability dated Jul. 5, 2011 in International Application No. PCT/US2009/069552; Written Opinion.

(56) References Cited

OTHER PUBLICATIONS

Office Action dated Jul. 13, 2011 in U.S. Appl. No. 12/559,563.
Int'l Preliminary Report on Patentability dated Sep. 1, 2011 in Int'l Application No. PCT/US2010/048556.
Office Action dated Sep. 6, 2011 in U.S. Appl. No. 12/345,818.
Office Action dated Feb. 21, 2012 in U.S. Appl. No. 12/689,249.
Int'l Search Report dated Jun. 17, 2011 in Int'l Application No. PCT/US2011/021604.
Int'l Search Report dated Oct. 12, 2011 in Int'l Application No. PCT/US2011/021605.
Office Action dated Oct. 28, 2011 in U.S. Appl. No. 12/615,828.
Int'l Search Report dated Sep. 22, 2011 in Int'l Application No. PCT/IL11/00368; Written Opinion.
U.S. Appl. No. 13/521,181 by Cabiri, filed Jul. 9, 2012.
U.S. Appl. No. 13/521,167 by Cabiri, filed Jul. 9, 2012.
Office Action dated May 16, 2012 in U.S. Appl. No. 12/615,828.
Office Action dated Jul. 2, 2012 in U.S. Appl. No. 13/272,555.
Office Action dated May 3, 2012 in CN Application No. 200880117084.X.
U.S. Appl. No. 13/429,840 by Cabiri, filed Mar. 26, 2012.

\* cited by examiner

Fig. 5

METHOD FOR SELECTIVELY POWERING A BATTERY-OPERATED DRUG-DELIVERY DEVICE AND DEVICE THEREFOR

BACKGROUND OF THE INVENTION

The present invention, in some embodiments thereof, relates to a selectively powered battery-operated device and, more particularly, but not exclusively, to a selectively powered battery-operated drug-delivery device, the device having a battery and a battery circuit.

It may be desirable to interrupt a battery circuit by placing, for example, a plastic tab along the battery circuit, for example, between a battery and en electrical contact or between a pair of batteries in series, thereby preventing the completion of an electrical circuit.

For example, U.S. Pat. No. 8,086,306 discloses a defibrillator device which has a removable tab disposed "between a battery terminal and an electrical contact inside the battery compartment." The tab serves as a battery isolator, for preventing draining of the battery when the device is not in use. When it is desired to operate the device, a "user pulls the tab to remove it from the battery compartment. This completes the circuit" so that the device may be used.

U.S. Pat. No. 6,336,729 teaches an emergency light device which is powered by a battery which forms part of a battery circuit. The battery circuit also includes a pair of contacts which are biased toward each other and between which a battery insulating member is disposed, thereby interrupting the battery circuit. The device also includes a cover to which is attached an activation button connected to the insulating member. When the cover is opened, the insulating member is removed from the battery circuit, thereby causing the device to be activated, whereby the light goes on.

Additional background art includes U.S. Pat. Nos. 5,645,955 and 5,795,675.

SUMMARY OF THE INVENTION

The present invention in some embodiments relates to apparatus for selectively powering a battery-operated drug-delivery device and a selectively powered battery-operated drug-delivery device, the device having a battery and a battery circuit.

The device may include features, for example, as shown in Applicant's U.S. Patent Applications Publication Nos. 2011/0178472, 2010/0168683, and 2011/0066131; U.S. Pat. No. 7,967,795; and WO Patent No. 2011/090955.

According to an aspect of some embodiments of the present invention there is provided a method for selectively powering a battery-operated drug-delivery device, the device having a battery and a battery circuit, the method comprising: providing a battery isolator disposed in a first position whereat the isolator contacts a battery terminal so as to interrupt the battery circuit, such that no power is provided to the device; and activating a fastening mechanism of the device, the fastening mechanism configured for fastening the device to the skin of a user, the activating causing movement of the battery isolator to a second position whereat the battery circuit is uninterrupted by the isolator, such that power is provided to the device.

According to some embodiments of the invention the fastening mechanism includes an adhesive surface; and the activating includes removing a protective cover from the adhesive surface.

According to some embodiments of the invention the providing includes providing a pre-attached isolator to the protective cover.

According to some embodiments of the invention the providing includes providing the isolator as an extension of the protective cover.

According to some embodiments of the invention the protective cover includes a tab configured to facilitate removal of the protective cover from the adhesive surface; and the activating includes pulling the tab so as to remove the protective cover from the adhesive surface.

According to some embodiments of the invention the protective cover includes a single portion configured to cover the adhesive surface; and the activating includes removing the protective cover so as to expose the entire adhesive surface.

According to some embodiments of the invention the protective cover includes at least two portions, each portion configured to cover a corresponding portion of the adhesive surface; the removing including removing a particular one of the at least two portions.

According to some embodiments of the invention the isolator is attached to a particular one of the at least two portions.

According to some embodiments of the invention the device includes a battery chamber and wherein, when the isolator is in the first position, the isolator is at least partially disposed in the battery chamber adjacent at least one of the at least one battery contact.

According to some embodiments of the invention, when the isolator is in the first position, the isolator is at least partially disposed between the at least one battery contact and a corresponding battery terminal of the battery located in the battery chamber; and the activating includes removing the isolator from between the at least one battery contact and the corresponding battery terminal of the battery located in the battery chamber.

According to some embodiments of the invention the battery circuit includes at least first and second batteries, the providing including providing the isolator in the first position whereat the isolator prevents a battery contact of the first battery from electrically contacting a battery contact of the second battery; the activating causing the isolator to be moved to the second position whereat the battery contact of the first battery electrically contacts the battery contact of the second battery.

According to some embodiments of the invention the device includes a battery chamber and wherein, when the isolator is in the first position, the isolator is at least partially disposed in the battery chamber adjacent at least one of the battery contact of the first battery and the battery contact of the second battery.

According to some embodiments of the invention, when the isolator is in the first position, the isolator is at least partially disposed in the battery chamber between the battery contact of the first battery and the battery contact of the second battery; the activating including removing the isolator from between the battery contact of the first battery and the battery contact of the second battery.

According to some embodiments of the invention the method further comprises: providing an additional battery isolator disposed in a first position whereat the additional isolator contacts a battery terminal so as to interrupt the battery circuit, such that no power is provided to the device; and activating an obstruction member of the device, the obstruction member configured for preventing a needle from projecting out of the device, the activating the obstruction member causing movement of the additional battery isolator to a second position whereat the battery circuit is uninterrupted by the additional isolator, such that power is provided to the device when the fastening mechanism is activated.

According to an aspect of some embodiments of the present invention there is provided a selectively powered battery-operated drug-delivery device, the device having a battery and a battery circuit, the device comprising: a selectively-removable isolator, the isolator disposed in a first position whereat the isolator contacts a battery terminal so as to interrupt the battery circuit, such that no power is provided to the device; the isolator configured to be movable to a second position whereat the battery circuit is uninterrupted by the isolator, such that power is provided to the device; and a fastening mechanism configured for fastening the device to the skin of a user, the fastening mechanism including a selectively removable portion, the battery isolator extending from the removable portion.

According to some embodiments of the invention the device comprises a housing, the housing including an opening through which the isolator extends when in the first position.

According to some embodiments of the invention the opening comprises a slot.

According to some embodiments of the invention the isolator extends from outside the housing, through the opening.

According to some embodiments of the invention the device further comprises a protective cover on the fastening mechanism, wherein the isolator extends from the protective cover, through the opening.

According to some embodiments of the invention the fastening mechanism includes an adhesive surface.

According to some embodiments of the invention the isolator is pre-attached to the protective cover.

According to some embodiments of the invention the isolator is an extension of the protective cover.

According to some embodiments of the invention the protective cover includes a tab configured to facilitate removal of the protective cover from the fastening mechanism.

According to some embodiments of the invention the protective cover includes a single portion configured to cover the entire the fastening mechanism.

According to some embodiments of the invention the protective cover includes at least two portions, each portion configured to cover a corresponding portion of the fastening mechanism.

According to some embodiments of the invention each of the at least two cover portions includes a tab configured to facilitate removal of the cover portion from the fastening mechanism.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

The present invention, in some embodiments thereof, relates to a selectively powered battery-operated device and, more particularly, but not exclusively, to a selectively powered battery-operated drug-delivery device, the device having a battery and a battery circuit.

In accordance with embodiments of the invention, there is provided a device including a fastening mechanism for fastening the device to the skin of a user configured such that activating the fastening mechanism results in movement of a battery isolator from a first position whereat the isolator interrupts a battery circuit, such that no power is provided to the device, to a second position whereat the battery circuit is uninterrupted by the isolator, such that power is provided to the device. This coupling of the battery isolator to the fastening mechanism has the potential advantage of providing the device with an easy to operate method of automatically powering up the device, which signifies imminent usage thereof, with little or no complicated preparation or activation protocols.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways, as discussed herein.

Figure 1:
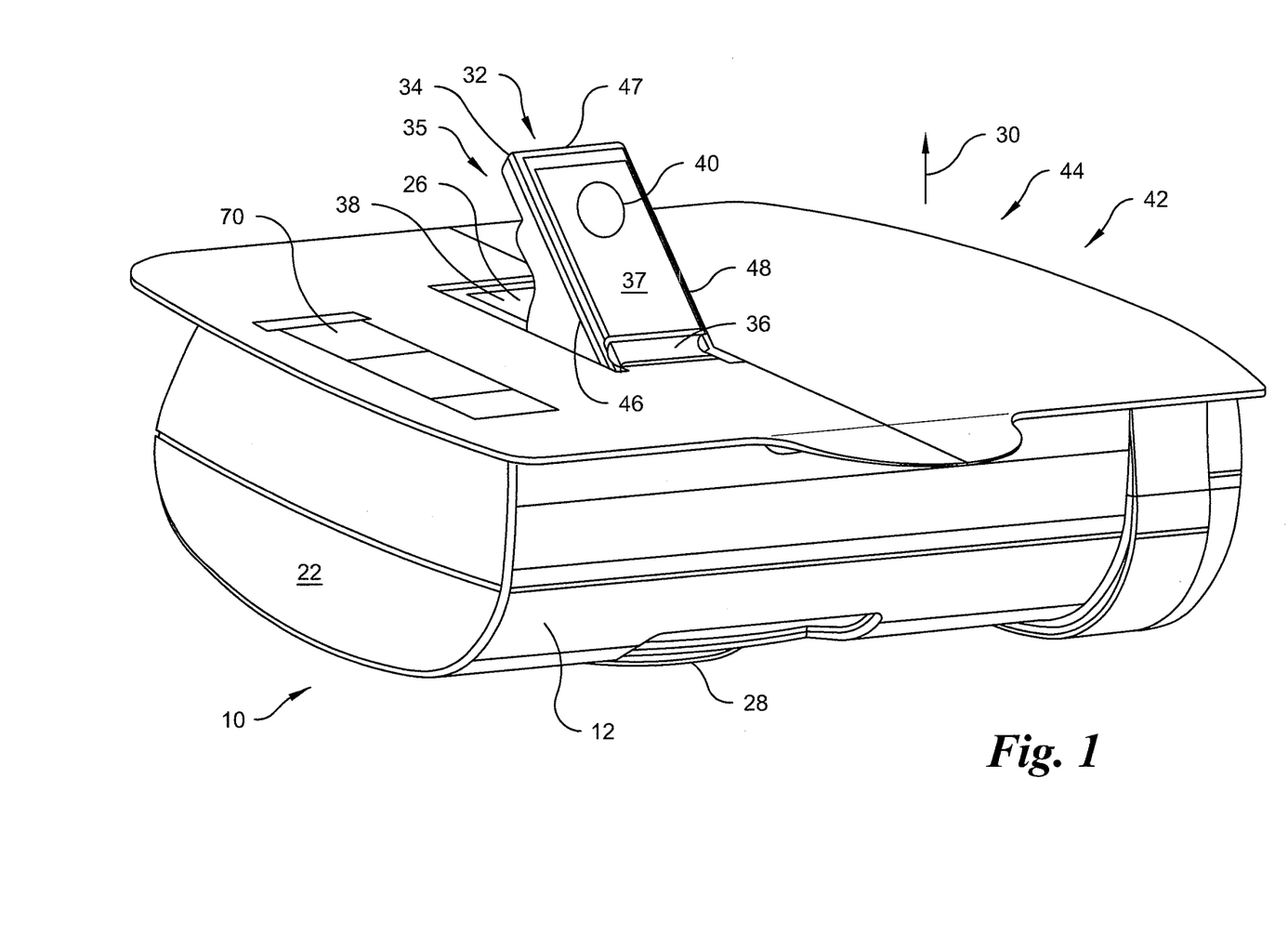
FIG. 1 is a perspective view of an automatic drug injection device having a battery isolator, in accordance with an exemplary embodiment of the present invention.

Referring now to the drawings, FIG. 1 illustrates an automatic drug injection device 10 having a battery isolator in accordance with the present invention. The automatic drug injection device 10 includes a housing 12 which is sized and shaped for housing a container such as a preloaded cartridge or a vial (not shown) of a drug to be injected by a user. Such a preloaded drug cartridge or vial may contain a volume of drug in the range of, for example, 0.7 ml-5 ml. Optionally, a drug cartridge or vial may contain any other volume of drug such as, for example, 10 ml.

As used herein, the term "drug" means any type of medicament, serum, or pharmaceutical composition which it may be desired to inject into a user. Additionally, as used herein, the term "delivery" means the transfer or conveyance of a drug from a device, by needle, into a user.

Figure 2:
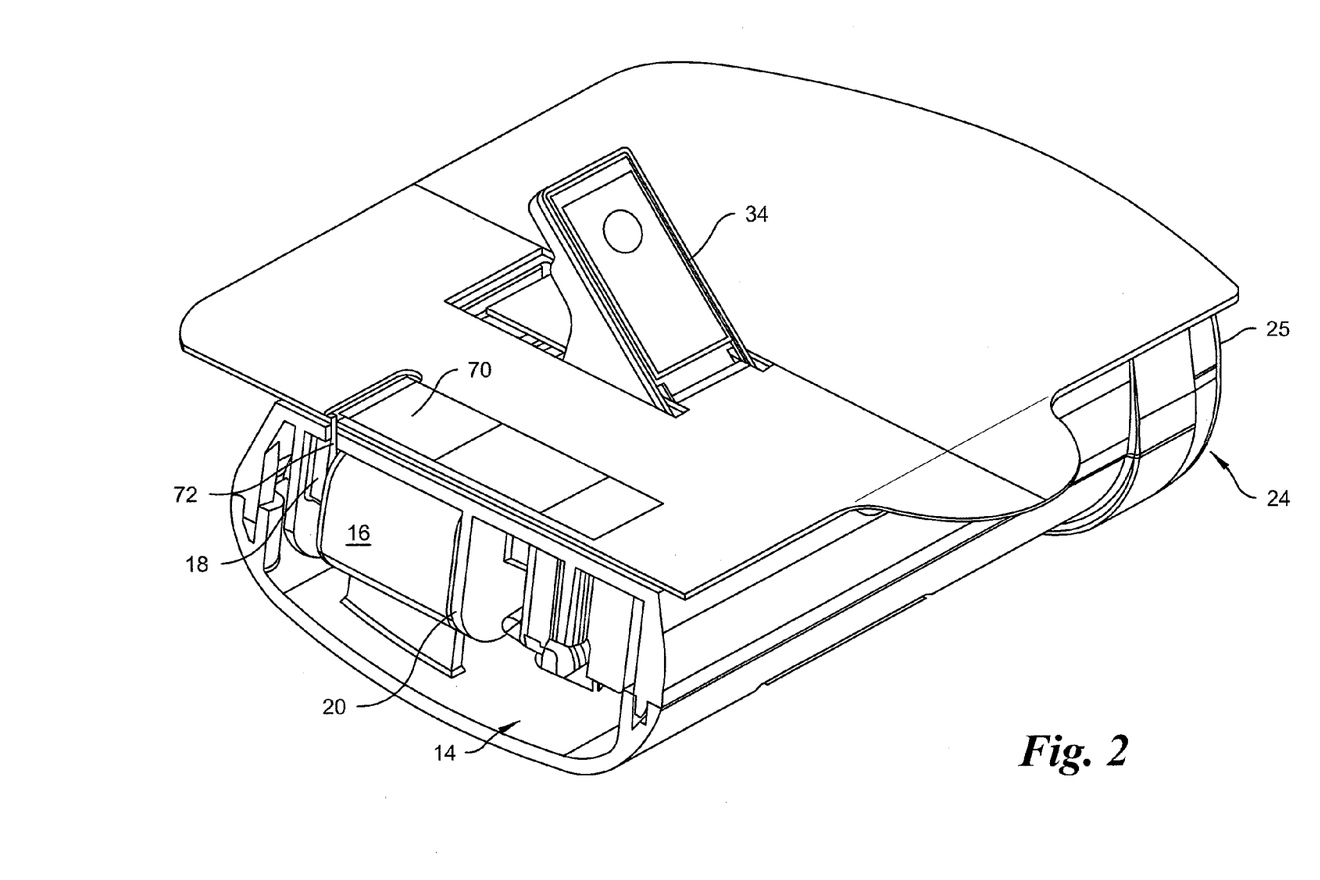
FIG. 2 is a perspective view of an exemplary embodiment of the drug injection device shown in FIG. 1, wherein the battery chamber cover has been removed.

With additional reference to FIG. 2, there is shown a drug injection device similar to that shown in FIG. 1, wherein a battery chamber cover 22 has been removed. Optionally, the device 10 has no battery chamber cover. As seen in FIG. 2, inside housing 12 there is provided a battery chamber 14, the chamber 14 configured for containing a battery 16 for powering the device. Battery 16 forms part of a battery circuit 17 (FIG. 4), as known in the art, and includes, in addition to battery 16, battery contact pads 18 and 20.

Optionally, instead of device 10 being powered by a single battery having a positive contact and a negative contact at opposite ends thereof, device 10 may be powered by a battery having a pair of contacts at one end thereof such as, for example, an Energizer 9V battery, model number EN22. Optionally, instead of a single battery, device 10 may include a battery circuit containing more than one battery in series or in parallel. Optionally, device 10 may be powered by at least one battery which is welded or otherwise fastened to a battery contact so as to be in electrical contact therewith.

Battery chamber 14 is provided with an optionally removable cover 22 (FIG. 1) which may be used to close the chamber 14. Cover 22 may be attached to housing 12 by any known means (not shown) such as, for example, screws, snap-in flanges, etc. Cover 22 is removable so as to allow the insertion and removal of battery 16 and closure of battery chamber 14.

Device 10 may be provided with a compartment 24 for housing a drug vial, as known in the art, the drug to be injected by a user via a needle 26, as will be discussed herein, in more detail. Compartment 24 may be provided with a cover 25 which, optionally, must be closed in order for the device to be operational, as discussed further herein.

Needle 26 is disposed within device 10 and may, for example, be flush with top side 42 thereof, and device 10 is provided with an actuation button 28 which, upon pressing thereof, causes needle 26 to be projected out of opening 38 in device 10 in the direction of arrow 30. Pressing of actuation button 28 also causes the drug in compartment 24 to be pumped out of device 10, via needle 26. The needle projection mechanism and pumping mechanism used may be any such mechanisms known in the art and will, therefore, not be described herein. It will, however, be appreciated by persons skilled in the art that either or both of projection of needle 26 out of device 10 and pumping of the drug via needle 26 may be powered by battery 16. Optionally, if desired, needle 26 may be spring loaded, such that pressing of actuation button or any other mechanism releases the needle 26, thereby allowing it to be projected out of device 10 by action of a spring mechanism (not shown), and only pumping of the drug via the needle 26 is powered by battery 16.

Device 10 may be provided with a safety mechanism 32 intended to prevent the possibly dangerous situation resulting from inadvertent projection of the needle, for example, in the case of the actuation button being pressed accidentally. Safety mechanism 32 includes an obstruction member 34 which, in the embodiment shown, is positioned approximately in the center of top side 42 of device. It will, however, be appreciated by persons skilled in the art that, if desired, obstruction member 34 may be located at any other position on top side 42 of device 10. Obstruction member 34 is hingedly attached to housing 12 at a biased hinge 36, the hinge 36 biasing the obstruction member 34 away from an opening 38 in housing 12. Obstruction member 34 is provided with a circular aperture 40.

The safety mechanism 32 is configured such that, when in the position shown in FIG. 1, pressing of actuation button 28 may cause the needle 26 to be projected out of opening 38 and to impinge upon inner surface 35 of obstruction member 34, thereby bending needle 26. Such bending of needle 26 may render it unusable.

If, however, the top side 42 (as shown in the drawings) of device 10 is placed on the skin of a user, such as when he wants to inject the drug into his skin, contact of the user with outer surface 37 of obstruction member 34 on device 10 causes member 34 to be moved toward opening 38, in the direction of arrow 44, such that member 34 is flush with the remainder of top side 42 of device 10, and aperture 40 coincides with the projection path of needle 26 out of device 10. In this manner, member 34 does not obstruct the path of needle 26 out of device 10 and into the user's skin.

Device 10 optionally includes a processor (not shown) for controlling operation thereof. Optionally, a processor may control any or all of the functions of the device including, for example, sensing the presence of a drug vial and projecting of a needle out of the device 10.

Figure 3:
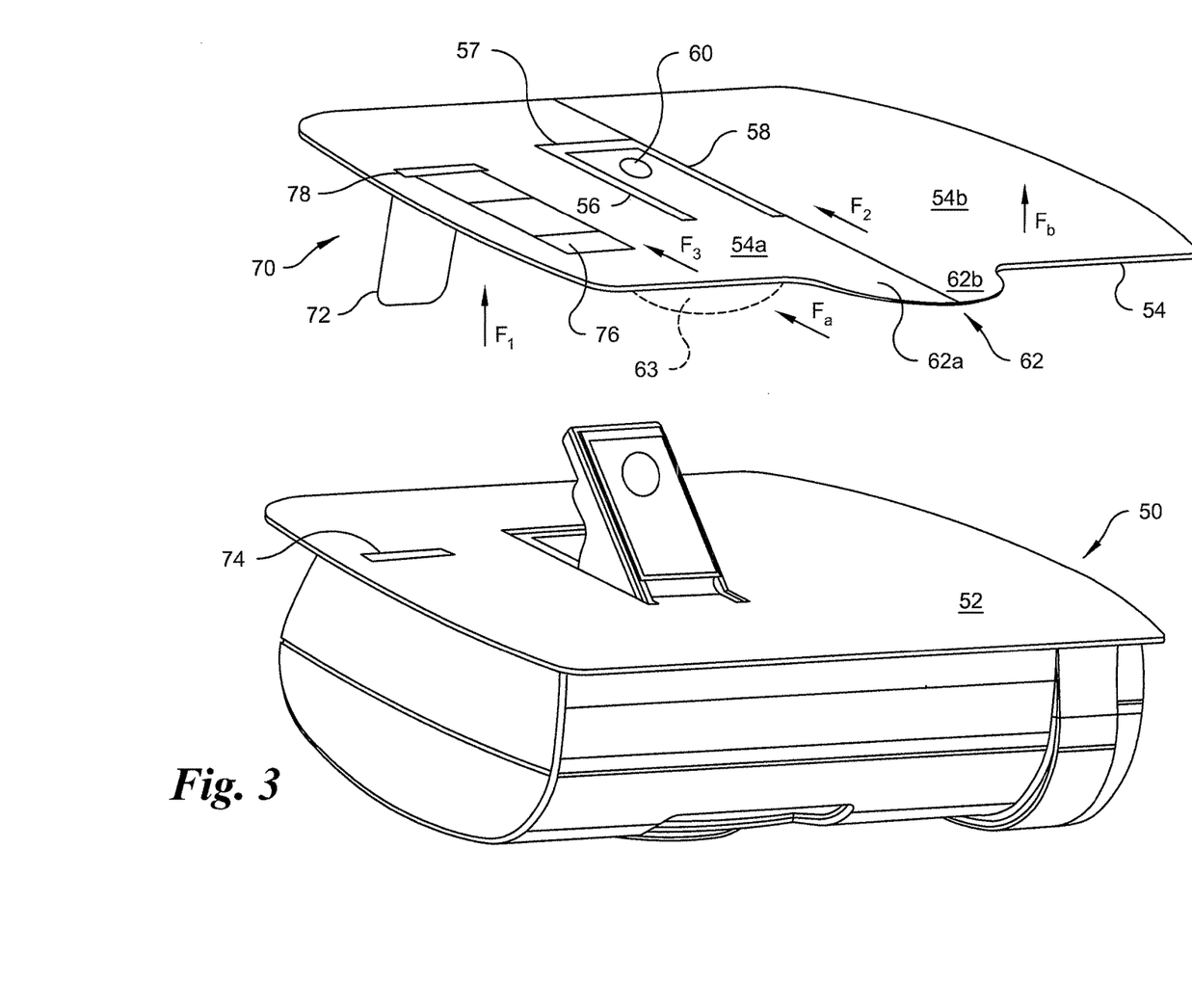
FIG. 3 is a perspective view of an exemplary embodiment of the drug injection device shown in FIG. 1, wherein the adhesive surface cover has been separated from the adhesive surface.

With additional reference to FIG. 3, device 10 is also provided with a fastening mechanism 50 on top side 42, the fastening mechanism defined by an adhesive surface 52. While adhesive surface 52 is preferably configured to cover the entire top side 42 of device 10, it will be appreciated by persons skilled in the art that, if desired, adhesive surface 52 may cover only a portion of top side 42 of device. The adhesive surface 52 may optionally also cover the outer surface 37 of obstruction member 34. Alternatively, if desired, adhesive surface 52 may not cover the outer surface 37 of obstruction member 34. Adhesive surface 52 is intended to steady the device 10 on the skin of a user and to allow the user to retain the device 10 on, for example, his arm, while pressing the actuation button 28 with his other hand.

Adhesive surface 52 is provided with a cover 54 which has a size and shape similar to adhesive surface 52 and may be fabricated from any suitable material such as, for example, paper, plastic, or a laminate. If, as mentioned above, the adhesive surface 52 also covers surface 37 of obstruction member 34, cover 54 is provided with slits 56, 57, and 58 which coincide with the location of the non-hinged outer edges 46, 47, and 48 of obstruction member 34 and aperture 40, respectively, and, similarly, cover 54 is provided with an aperture 60 which coincides with aperture 40 in obstruction member 34.

As shown in the drawings, cover 54 may be fabricated of two separate cover portions 54a and 54b, each corresponding to a portion of adhesive surface 52. Such a configuration may be advantageous as it may render cover 54 easier to remove from adhesive surface 52. Additionally, providing a cover 54 having a plurality of separate portions may facilitate removal of the cover without its tearing. The provision of a cover formed of two separate cover portions 54a and 54b may provide additional advantages, as discussed further below. Alternatively, if desired, cover 54 may be fabricated of a single piece of material.

Cover 54 may be provided with a cover tab 62 which may facilitate removal of cover 54 from adhesive surface 52. Tab 62 may be formed as an extension of cover 54 and may, as in the embodiment shown, include separate cover tab portions 62a and 62b on separate cover portions 54a and 54b, respectively.

In accordance with an embodiment of the invention, device 10 is provided with a selectively-removable battery isolator 70. As shown in FIGS. 2 and 3, battery isolator 70 has an L-shaped configuration, including a first portion 72 disposed inside housing 12, inside battery chamber 14, between battery 16 and contact pad 18, and a second portion 76 which, in the embodiment shown, is attached to the top of adhesive cover 54, as discussed further herein. Battery isolator 70 prevents electrical contact between battery 16 and contact pad 18, thereby interrupting the battery circuit 17 of device 10, such that no power is provided to the device 10. Optionally, if desired, device 10 may be constructed such that battery isolator 70 is located at any other point along circuit 17, thereby interrupting the supply of power to device 10.

Contact pad 18 may be biased toward battery 16, thereby applying pressure in the direction of battery 16. In the embodiment shown, due to the disposition of battery isolator 70 in between battery 16 and contact pad 18, pressure will be applied by contact pad 18 to isolator 70, in the direction of battery 16.

As shown in FIGS. 1-3, L-shaped battery isolator 70 extends from inside battery chamber 14, out of an opening 74 in the top side 42 of housing 12, and terminates in a second portion 76. Isolator 70 also passes through an opening 78 in cover 54 and is fastened, for example, by gluing or welding, to the cover 54.

Optionally, instead of battery isolator 70 being attached to cover 54, battery isolator 70 may be attached to a portion of material in which the device 10 may be packaged such as, for example, protective wrapping material or blister packaging. In this manner, when a device 10 is unwrapped or when the packaging in which the device 10 is opened or removed, the battery isolator 70 may be removed from the battery chamber 14, thereby providing power to the device 10.

Isolator 70 may be fabricated of any material such as, for example, plastic, PET (polyethylene terephthalate), polycarbonate layers, or a combination thereof. Isolator 70 may be fabricated of the same material as cover 54 or, optionally, may be fabricated of a different material from that of cover 54. Preferably, in order to facilitate the removal of isolator 70 from the housing 12, the particular material may possess properties which will allow the isolator to easily slide out of the opening 74 in housing 12. For example, the thickness of the isolator may be chosen such that it has an amount of flexibility so as to allow it to easily slide out of opening 74. The thickness of the isolator may be, for example, in the range of 0.05-0.15 mm.

Figure 4:
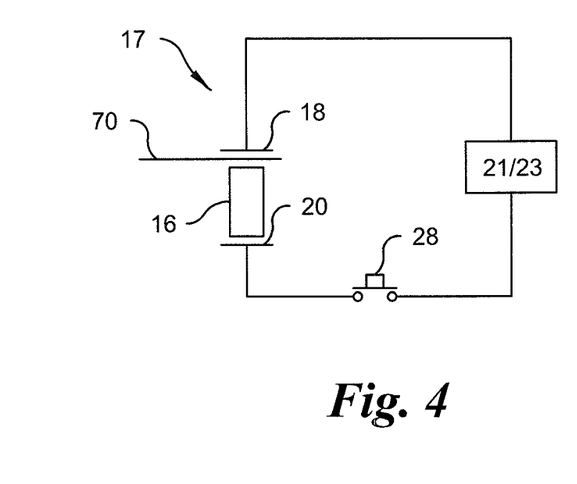
FIG. 4 is a schematic drawing of an exemplary embodiment of a battery circuit employing a battery isolator, in accordance with the present invention.

Additionally, first portion 72 of isolator 70 may be formed at least in part of a non-conductive material, at least at the portion thereof which is disposed along the battery circuit 17 such that it will interrupt the battery circuit, as discussed herein with reference to FIG. 4. Also, first portion 72 may be formed of a material that will not absorb moisture so as to render it electrically conductive.

It should be noted that, in the embodiment shown, each of openings 74 and 78 is in the form of a slot, the slot sized and shaped to accommodate the battery isolator, while providing it with an unobstructed pathway via which it may be easily removed from the housing by pulling up on the adhesive cover 54, as discussed further herein.

While, in the embodiment shown, each of openings 74 and 78 is in the form of a slot, it will be appreciated by persons skilled in the art that, if desired, any other shaped opening may be provided through which battery isolator 70 extends.

Optionally, if desired, instead of battery isolator 70 being formed as a separate piece that is fastened to the top of cover 54, battery isolator may be formed as a separate piece that is fastened to the bottom of cover 54. Alternatively, isolator 70 may optionally be formed as an extension of cover 54 and extend through opening 74 into battery chamber 14, as discussed herein. For example, during manufacture of cover 54, an extra portion of material from which the cover is formed may be left attached thereto, this extra portion of material then folded over, for example at a right angle to the cover, thereby forming an extension of the cover, the extension corresponding to first portion 72 of battery isolator 70.

As noted above, the provision of separate cover portions 54a and 54b on adhesive surface 52, each cover portion having a tab portion 62a and 62b, respectively, is particularly advantageous over the provision of a one-piece cover having a single tab, as discussed herein. Additionally, the particular location along the cover at which it is divided into separate portions may be significant, as will be discussed further herein. In particular, the removal of cover 54 from the adhesive surface 52, which results in removal of isolator 70 from housing 12 in accordance with embodiments of the present invention, requires a user to pull up on at least one tab, thereby applying a force to the cover (or a force to each cover portion) in a particular direction. The direction of the force applied to the cover (or cover portions) will be a combination of its components, i.e., the direction of upward pull of the tab 62 (or tab portions 62a and 62b) and the direction in a plane parallel to the adhesive surface 52 in which the cover (or cover portion) is removed.

It will be appreciated by person skilled in the art that, due to the L-shaped configuration of the battery isolator 70 and the disposition of isolator first portion 72 inside housing 12, removal of first portion 72 from the housing 12 may require that a force be applied to first portion 72 having a component in a direction $F_1$ (FIG. 3) which is substantially perpendicular to the adhesive surface 52.

If, for example, a single tab 62 on a one piece-cover 54 were positioned at the same location as shown for the two-piece tab (62a and 62b) shown in FIG. 3, in order to remove the adhesive cover 54 from the adhesive surface 52, a user may apply an upward force having a component in a direction $F_2$ along the approximate center of the cover. As adhesive cover 54 is removed from adhesive surface 52, before first portion 72 of the isolator 70 is removed from housing, the second portion 76 of isolator 70 will be raised above the plane of the adhesive surface 52, together with the cover 54. As the user continues to pull up on the tab, due to the L-shaped configuration of isolator 70, removal of the portion of the cover 54 which includes the isolator second portion 76 may require the user to pull the tab upward in a direction away from the isolator, thereby twisting first portion 72 inside the housing and/or the opening 74, and thereby possibly jamming the isolator 70 inside the housing 12 and/or the opening 74. Also, due to pressure that may be applied by contact pad 18 to isolator 70, as discussed above, an additional force may be required to remove the isolator 70 from the housing, the application of this additional force causing the isolator 70 to be further twisted and/or jammed inside the housing 12 and/or the opening 74.

Optionally, there may be provided a tab, indicated by dotted lines and ref. no. 63, nearer battery isolator 70 than tab 62 shown in FIG. 3, so as to facilitate the removal of battery isolator 70 from device 10. Alternatively, the tab maybe located in the area of any other spring contact like between the batteries or the Anode side or the contact to PCB itself. All the options are acting electronically the same but may select due to mechanical constrain of specific. Specifically, in order to remove the isolator 70 from the housing 12, a force having a component in the direction of $F_1$ is required in order to pull battery isolator 70 out of device 10, as noted above. Therefore, by positioning a tab 63 along the same side of the adhesive cover 54 as tab 62, but closer to the isolator 70, a user removing the cover 54 may apply an upward force having a component in the direction of $F_2$, but closer to isolator 70, for example, in the direction $F_3$. Therefore, as adhesive cover 54 is removed from adhesive surface 52, before first portion 72 of the isolator 70 is removed from housing, the second portion 76 of isolator 70 will be raised above the plane of the adhesive surface 52, together with the cover 54. As the user continues to pull up on the tab 63, due to the fact that the upward force applied to tab 63 is in the direction of the isolator and has components in the directions of $F_1$ and $F_3$, removal of the portion of the cover 54 which includes the isolator second portion 76 is facilitated, thereby preventing twisting and/or jamming of first portion 72 inside the housing and/or the opening 74.

Alternatively, if desired, instead of providing adhesive surface 52 with a one-piece cover 54 having a single tab thereon, a pair of cover portions 54a and 54b may be provided, whereby each cover portion is provided with a respective tab portion 62a and 62b. This configuration of the cover may facilitate removal of the isolator 70 from device 10, while preventing its twisting and/or jamming, as discussed herein. In particular, as shown in FIG. 3, due to the provision of two separate tab portions 62a and 62b, in accordance with embodiments of the invention, for each tab portion the user may apply an upward force, each having a respective component, $F_a$ and $F_b$, each in a direction of the approximate center of the respective tab portion. For cover portion 62a, to which isolator 70 may be fastened, application of an upward force having a component $F_a$ to tab portion 62a will achieve removal of cover portion 54a from adhesive surface 52. As cover portion 54a is removed, the tab portion 62a may be pulled upward in a direction toward the isolator 70. Before first portion 72 of the isolator 70 is removed from housing 12, the second portion 76 of isolator 70 may be raised together with cover portion 54a above the plane of the adhesive surface 52 until it is substantially perpendicular thereto. As the user continues to pull tab portion 62a upward, the cover portion 62a is pulled by a force having components in the directions $F_a$ and $F_1$, whereby the isolator will be removed from opening 74 without twisting and/or jamming therein.

It will be appreciated by persons skilled in the art that, in addition to the provision of separate cover portions 54a and 54b, the particular point of division of the cover 54 into separate portions may be chosen such that the cover portions may be removed without the isolator becoming twisted and/or jammed in the device, as discussed above.

As noted above, the particular slot size and width of opening 74 in housing 12 and opening 78 in cover 54 may be chosen so as to prevent twisting and/or jamming of the isolator portion 72 inside the housing 12, thereby facilitating its removal from the device 10. Preferably, an isolator first portion 72 may be 10 mm wide by 30 mm long, wherein the width corresponds substantially to a battery diameter and the length corresponds to a length allowing the isolator to extend out of the housing 12 and onto the cover 54. Opening 74 may be wider than the width of isolator first portion 72. For example, opening 74 may be approximately 2 mm wide. Also, opening 74 may have a thickness which is substantially greater than that of the isolator first portion 72. The thickness of opening 74 may be, for example, 1 mm.

Figure 5:
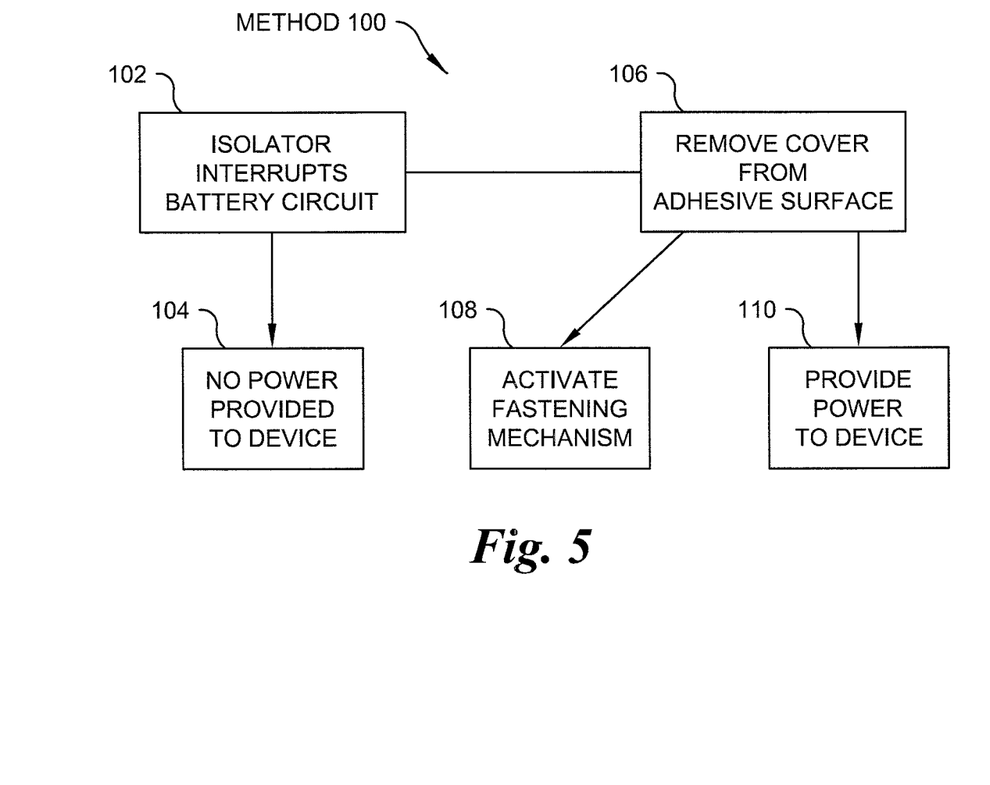
FIG. 5 is a flowchart illustrating an exemplary embodiment of a method for selectively powering a battery-operated drug-delivery device, in accordance with the present invention.

FIG. 5 illustrates a method 100 for selectively powering a battery-operated drug-delivery device having a battery circuit and injecting the drug into a user, in accordance with the present invention. The results of actions according to the method are also illustrated. According to the method 100, as shown at 102, a battery isolator is in a first position, whereat it interrupts the battery circuit. As a result of the battery circuit being interrupted, no power is provided to the device, as shown at 104. As shown at 106, removal of a cover from an adhesive surface of the device causes a fastening mechanism of the device to be activated, as shown at 108, whereby the device may be fastened to the skin of a user. Removal of the adhesive cover also causes movement of the battery isolator to a second position whereat the battery circuit is uninterrupted by the isolator, such that power is provided to the device, as shown at 110. Optionally, after removal of the adhesive cover together with the battery isolator, if desired, the adhesive cover together with the battery isolator may be discarded.

It should be noted that the simple mechanical action 106 of removing the cover 54 from the device 10 results in completion of the battery circuit 17 (FIG. 4). This provides the device with an easy to use method of powering the device, as will be appreciated by persons skilled in the art. Once power has been supplied to the device, it may be operated as required for the injection of a drug. Specifically, once power has been supplied to the device, a user may press on the actuation button 28 (FIG. 1), thereby causing a needle to be projected out of the device and causing a drug to be pumped out of the device, as discussed herein. As discussed above, operation of device 10 may be controlled by a processor or, optionally, device 10 may not include a processor.

As discussed above, the present invention, in embodiments thereof, provides an isolator 70 which may be attached to the cover 54 (or cover portions 54a and 54b) of the adhesive surface 52, thereby providing a user with a simple mechanism for removing the isolator 70 while fastening the device 10 to his skin. Therefore, aside from removing the cover 54 from the adhesive surface 52, which is an action required to operate the device 10, there are no additional actions that the user is required to perform. The invention, in embodiments thereof, therefore provides a simple, effective mechanism for completing a battery circuit of a device.

Optionally, in addition to device 10 being provided with battery isolator 70, the device may be additionally provided with a second battery isolator (not shown), thereby requiring the removal of both isolator 70 and the second battery isolator in order to power the device. For example, an additional battery isolator may be attached to or continuous with obstruction member 34 (FIG. 1), in a manner similar to that discussed herein with regard to isolator 70. Therefore, both the action of pressing down on the obstruction member 34 (FIG. 1), and the action of removing adhesive cover 54 (or cover portion 54a), as discussed herein, may be required in order to complete battery circuit 17 (FIG. 4), thereby powering device 10.

It will be appreciated by persons skilled in the art that, in accordance with embodiments of the present invention, any combination of actions required to operate device 10, such as the actions of removing the adhesive cover, pressing down on the obstruction member 34, pressing of an actuation button 28, and closing cover 25 on drug vial compartment 24 may be required in order to power the device 10. It should be noted that, by requiring these actions, either individually and in combination, in order to power the device, as discussed herein, device 10 is provided with a simple mechanism for selectively completing battery circuit 17, requiring no action in order to remove battery isolator 70 from the device 10, other than the action(s) required to operate the device 10.

It is expected that during the life of a patent maturing from this application many relevant battery isolators will be developed and the scope of the term battery isolator is intended to include all such new technologies a priori.

The terms "comprises", "comprising", "includes", "including", "having" and their conjugates mean "including but not limited to."

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A selectively powered battery-operated drug-delivery device comprising:

a unitary housing having a battery and a complete battery circuit therein;

a needle disposed within said housing and projectable at least partially out of said housing for administering a drug within said housing to a user;

a selectively-removable isolator, said isolator disposed in a first position whereat said isolator contacts a battery terminal within said housing so as to interrupt the complete battery circuit, such that no power is provided to the device;

said isolator configured to be movable to a second position whereat the complete battery circuit is uninterrupted by said isolator, such that power is provided to the device; and an adhesive surface disposed along a side of the unitary housing, configured for fastening the device to the skin of the user, said adhesive surface being provided with a selectively removable protective cover, said isolator being an integral extension of the protective cover extending into the housing in the first position, whereby removal of the protective cover moves the isolator from the first position to the second position, thereby connecting the complete battery circuit to provide power to the device.

2. A device according to claim 1, wherein said housing includes an opening through which said isolator extends when in said first position.

3. A device according to claim 2, wherein said opening comprises a slot.

4. A device according to claim 2, wherein said isolator extends from outside said housing, through said opening.

5. A device according to claim 1, wherein said protective cover includes a tab configured to facilitate removal of the protective cover from said adhesive surface.

6. A device according to claim 1, wherein said protective cover includes a single portion configured to cover the entire said adhesive surface.

7. A device according to claim 1, wherein said protective cover includes at least two portions, each portion configured to cover a corresponding portion of said adhesive surface.

8. A device according to claim 7, wherein each of said at least two cover portions includes a tab configured to facilitate removal of the said cover portion from said adhesive surface.

9. A device according to claim 2, further comprising an actuation button for projecting the needle at least partially out of the housing for engaging the skin of the user and pumping the drug out of the housing via the needle upon pressing thereof, wherein said actuation button is powered by said battery.

* * * * *